United States Patent [19]

Pavel

[11] Patent Number: 4,777,952
[45] Date of Patent: Oct. 18, 1988

[54] DEVICE AND METHOD OBTAINING AN AUDIBLE INDICATION OF EEG IN CONJUNCTION WITH ELECTROCONVULSIVE THERAPY

[75] Inventor: John Pavel, Islip Terrace, N.Y.

[73] Assignee: Somatics, Inc., Lake Bluff, Ill.

[21] Appl. No.: 815,209

[22] Filed: Dec. 31, 1985

[51] Int. Cl.⁴ ............................................. A61N 1/36
[52] U.S. Cl. ............................... 128/419 S; 128/731
[58] Field of Search .......... 128/419 D, 419 R, 419 S, 128/701, 731, 732, 741

[56] References Cited

U.S. PATENT DOCUMENTS

| | | | |
|---|---|---|---|
| 3,527,228 | 9/1970 | McLaughlin | 128/419 D |
| 3,753,433 | 8/1973 | Bakerich et al. | 128/732 |
| 4,170,225 | 10/1979 | Criglar et al. | 128/732 |
| 4,228,807 | 10/1980 | Yagi et al. | 128/732 |
| 4,331,157 | 5/1982 | Keller, Jr. et al. | 128/696 |

*Primary Examiner*—William E. Kamm
*Attorney, Agent, or Firm*—Eugene F. Friedman

[57] ABSTRACT

An audible electroencephalograph (EEG) for use with electroconvulsive therapy (ECT). A voltage controlled oscillator converts the magnitude of the signal received from the patient's brain into an audible tone indicative of brain activity. The tone undergoes frequency modulation about 500 hertz to indicate to the attending physician the brain seizure produced by the ECT. The audible signal informs the physician of the results of the ECT without requiring any attention to or waiting for a strip recorder to provide a graphic display. This permits the physician to continuously watch the patient during the ECT. Used in conjunction with the ECT equipment, a first, warning tone may indicate a short hiatus between pressing the treatment button and the commencement of the ECT stimulus. A second tone indicates the application of the ECT stimulus, while the third tone, as described above audibly delineates the resulting effect upon the patient.

25 Claims, 5 Drawing Sheets

DEVICE AND METHOD OBTAINING AN AUDIBLE INDICATION OF EEG IN CONJUNCTION WITH ELECTROCONVULSIVE THERAPY

BACKGROUND

Electroconvulsive therapy (ECT), more colloquially known as electric shock treatment, finds use in modern psychiatry for patients suffering from severe depression or melancholia. A description of the indications for ECT as well as present techniques appears in the booklet *Thymatron TM Instruction Manual* by Richard Abrams, M.D., and Conrad Swartz, Ph.D., M.D., (May 1985), published by Somatics, Inc., 910 Sherwood Drive, Unit 18, Lake Bluff, Ill. 60044, and the references cited there.

During ECT, the patient remains under anesthesia. Accordingly, he may exhibit no physical movement during the seizure induced by the ECT. Accordingly, the physician should follow the course of treatment through information provided by an electroencephalogram (EEG) taken during treatment.

The ECT, to produce the required therapeutic effect, should generally produce a seizure which lasts at least 25 seconds. If the seizure lasts less than this time, the physician often repeats the ECT with a larger electrical dosage to achieve the therapeutic benefit for the patient.

The EEGs currently in use provide a readout of the patient's brain activity drawn by a line on a strip of paper. To obtain this information, the physician must direct and keep his attention to the recoder producing the graph. To the extent that he does so, he can not devote his undivided attention to the patient undergoing the ECT or to his vital signs. Also, only one person can usually review the graph.

Additionally, the mechanism for driving the paper becomes subject to the normal wear and tear through time. It may, in fact, prove unworkable when actually needed during ECT.

Furthermore, the equipment utilizes electroencephalograph paper. This of course, must undergo replacement at regular, frequent intervals.

Also, interpreting the paper EEG record requires substantial sophistication and technical expertise. Moreover, it requires time to study the graph in order to arrive at a determination as to the effectiveness of the ECT.

SUMMARY

Providing the results of EEG in audible form will permit the instantaneous following of the course of the ECT treatment by an attending physician. Moreover, he will not have to remove his attention from the patient in order to obtain this vitally needed information.

To produce the audible tone, the EEG device should include a transducer which detects the brain activity of a patient. The transducer, based on the information it receives from the patient, produces a first electrical signal external to that patient. The signal, of course, has an amplitude proportional to the magnitude of the detected brain activity.

A converter then couples to the transducer and produces a second electrical signal having an a.c. character. The second signal has a frequency defined as a function of the amplitude of the first signal produced by the transducer.

An audibilizer represents a third component of the EEG device and couples to the converter. The audibilizer converts the second electrical signal to an audible signal reflective of the second electrical signal's frequency.

Typically, the resulting audible tone has a frequency equal to the a.c. signal produced by the converter. As the magnitude of the detected brain activity varies, so will the frequency of the second electrical signal produced by the converter and thus the tone generated by the audibilizer. The physician then listens to the tone and obtains a direct indication of the patient's brain activity during a seizure induced by ECT.

The method of discerning the effect of electroconvulsive therapy upon a patient commences with the detection of the brain activity of a patient. The method then requires the producing of a first electrical signal having an amplitude proportional to the magnitude of the brain activity detected in the patient.

From the first electrical signal, a second a.c. electrical signal must result which will have a frequency defined as a function of the amplitude of the first signal. Lastly, the second electrical signal should undergo conversion to an audible signal. This last audible signal must indicate the frequency of the second electrical signal and, thus, the magnitude of the induced brain activity.

DETAILED DESCRIPTION

Figure 1:
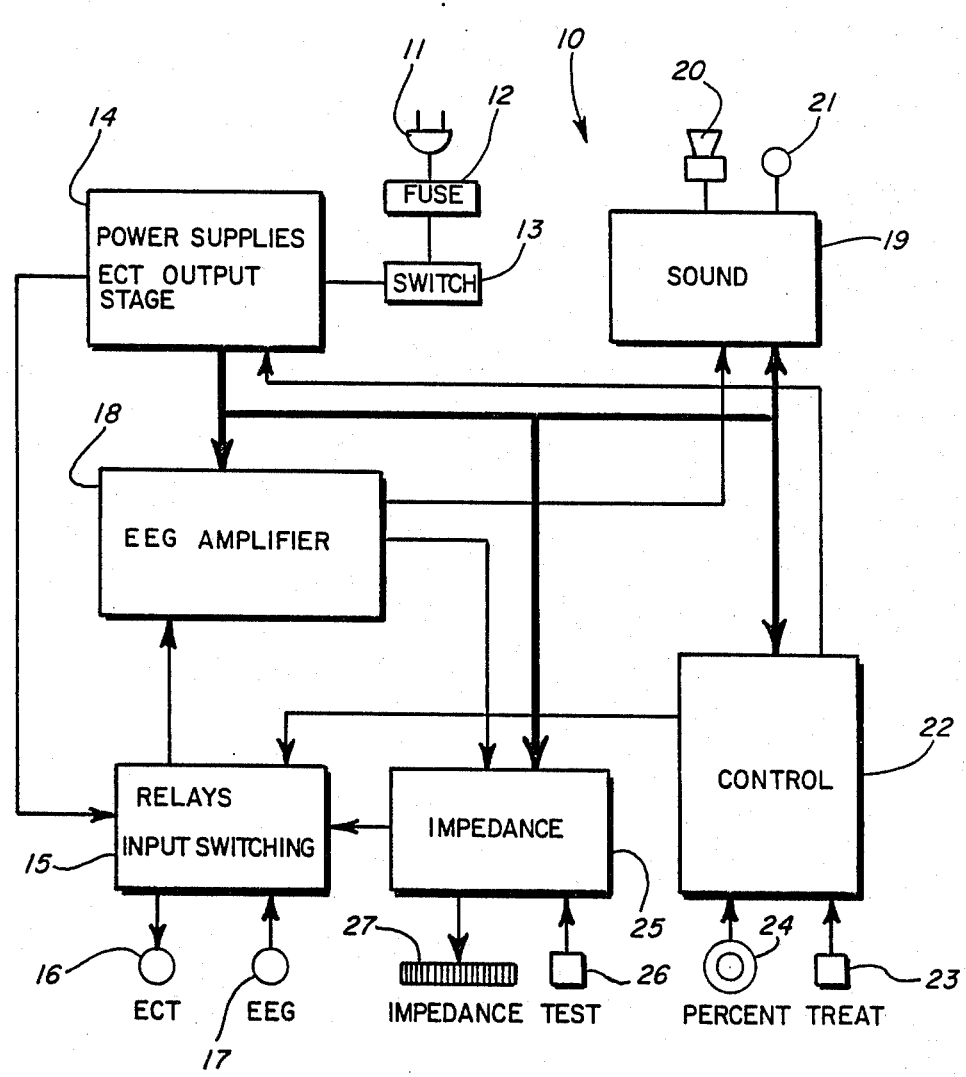
FIG. 1 gives a block diagram of EEG-ECT equipment providing an audible electroencephalograph.

FIG. 1 shows a block diagram generally at 10 for an ECT-EEG device that will produce an audible EEG. Naturally, the diagram includes the plug 11 for receiving the usual a.c. mains current, the fuse 12, and the on-off switch 13.

The power supply block 14 provides the necessary voltage and current for the remaining portions of the instrument. It also delivers the electrical current required for the actual ECT. The current for ECT passes to the box 15 which includes the relays and the input switching which connects the power to the ECT leads 16 attached to the patient.

After the application of the ECT electricity, the brain exhibits drastically altered electrical activity detected by the EEG leads 17. After passing back through the switching box 15, the EEG signal travels to the EEG amplifier 18 and then the sound box 19 which provides the audible tone on the loudspeaker 20. The volume control knob 21 permits the physician to adjust the volume to an acceptable level.

The control of the circuits shown in FIG. 1 occurs in the box 22. To initiate an ECT, the physician depresses the treatment button 23. This induces the remainder of the circuit to provide ECT and determine the results through the EEG section. The percentage knob 24 on the control box 22 determines the amount of electrical shock received by the patient.

Lastly, prior to the patient actually undergoing ECT, the impedance between the electrodes placed on his head should be tested. The equipment shown in FIG. 1 does this through the impedance box 25. The physician presses the test button 26 and obtains a reading of the patient's impedance through the meter 27. A low impedance generally will indicate a short circuit between the electrodes through, for example, wet hair on the patient.

Figure 2:
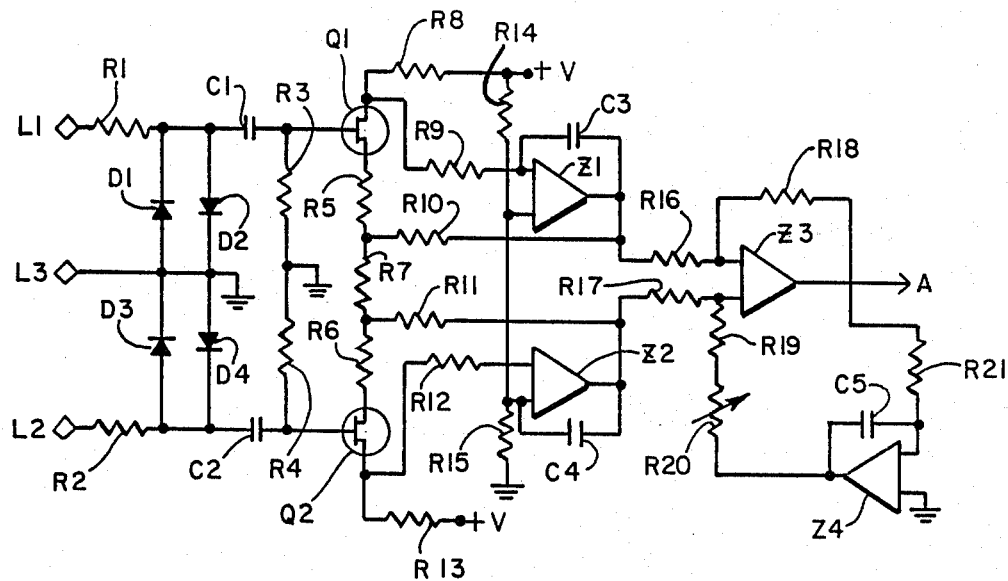
FIG. 2 shows the leads and the differential amplifier circuit of the audible EEG section of the equipment shown in FIG. 1.

In FIG. 2, the EEG leads L1 and L2 attach to the patient over the front of the forehead. These, of course, detect the brain's electrical activity. The ground lead L3 attaches to a location of the patient's body remote from his head, for example his shoulder.

The EEG becomes effective after the application of the ECT stimulus. A switching mechanism in the instrument prevents the operation of the EEG during ECT stimulus.

Furthermore, as discussed below, the equipment itself produces three different sounds. When the physician depresses the treatment button to commence the ECT, the instrument gives a warning sound for approximately one second. During this time, the patient receives no ECT. If the physician releases the button during this period of time, no ECT results.

However, if the physician continues to depress the treatment button beyond the duration of the warning, then ECT commences. A second tone, appreciably different from the warning sound, emanates from the equipment during the actual ECT stimulus.

At the termination of the ECT stimulus, the instrument switches to the EEG mode to determine the effect of the ECT. It then emits a tone indicative of the actual course of the brain activity of the patient subsequent to the ECT stimulus.

Returning to FIG. 2, the diodes D1 to D4 and the resistors R1 and R2 protect the EEG amplification electronics for the ECT stimulus. Otherwise, the voltage from the ECT stimulus could damage the remaining components.

FIG. 2 provides a low-noise differential amplifier for the difference in the signals received by the leads L1 and L2. The field-effect transistors Q1 and Q2 amplify the signal while providing a high input impedance. The operational amplifiers Z1 and Z2 provide negative feedback to the FETs Q1 and Q2 for stability.

At the right end of FIG. 2, the operational amplifier Z3 produces, as its output, a single signal characteristic of the difference between the two input signals derived ultimately from the leads L1 and L2. The output, appearing on the lead A, then travels to the circuit shown in FIG. 3. In FIG. 2, the positive voltage +V appears at +15 volts while, in the other figures, the negative voltage −V stands at −15 volts.

In FIG. 2, the circuitry amplifies the signal 1000 times through the low-noise, differential amplifier. The amplifier has a 2 to 3000 thousand Hertz band width and a common mode rejection of 80 dB.

Figure 3:
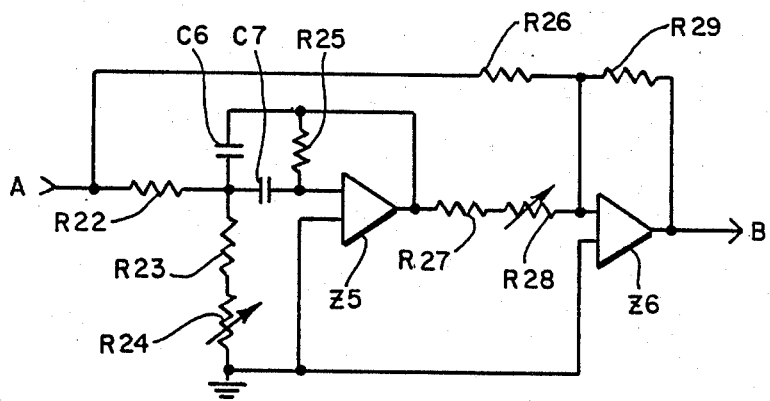
FIG. 3 gives the notch filter circuit of the EEG section of the equipment shown in FIG. 1.

The circuitry in FIG. 3 simply operates as a notch filter to remove any 60 Hertz signal. This frequency corresponds to the usual house current. The output of FIG. 3, on this lead B, appears at the input of FIG. 4.

Figure 4:
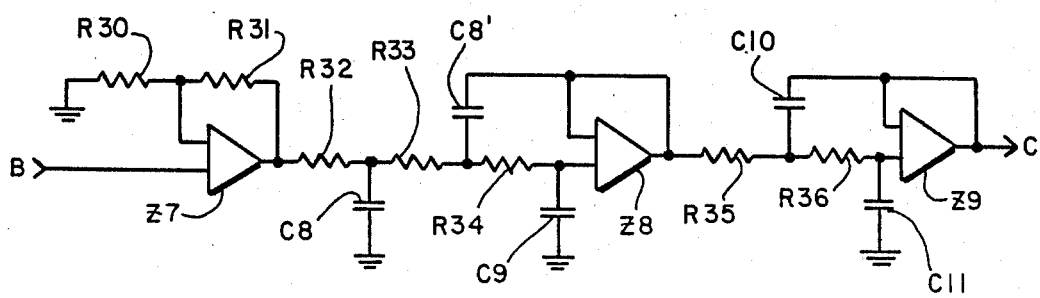
FIG. 4 shows the amplifier and the low-pass filter circuitry of the EEG section of the equipment of FIG. 1.

The signal, in FIG. 4, receives amplification by a factor of 10. It then enters a 0 to 25 Hertz low-pass filter which includes the operational amplifier Z9. The operational amplifier has a 30 dB per octave rolloff.

Figure 5:
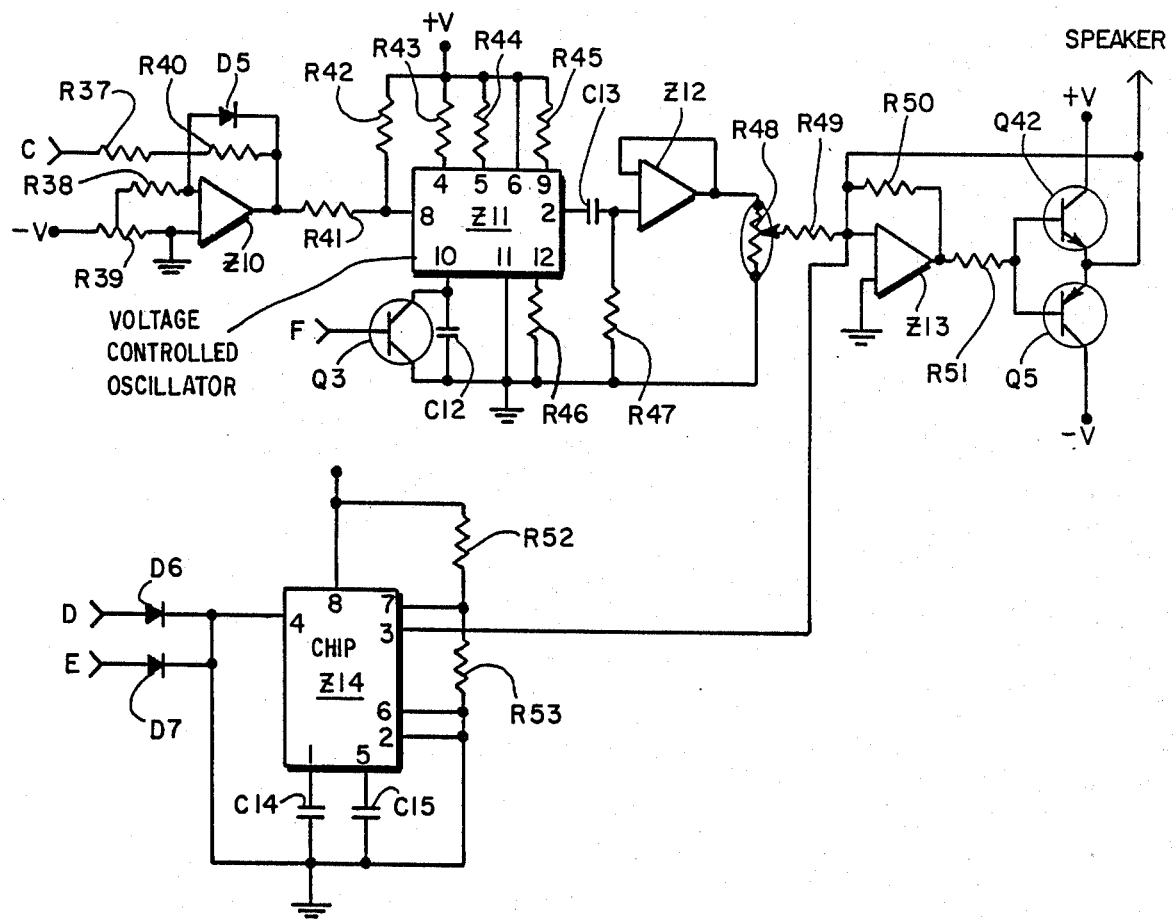
FIG. 5 displays the EEG oscillator and ECT warning and therapy-application tone generator as well as the audio amplifier circuit of the equipment shown in FIG. 1.

The signal produced by the circuitry of FIG. 4 on the lead C enters FIG. 5. At this point, it takes the characteristics of a normal EEG signal. The signal passes to the voltage controlled oscillator Z11 which first generates a 500 Hertz audio carrier wave. Generally, the carrier wave should fall in the easily audible range of about 200 to 1000 Hertz. The oscillator Z11 also acts as a voltage-to-frequency convertor, transforming the amplitude of the voltage to a modulation of the 500 Hertz audio carrier to produce the audible tone. The potentiometer R48 permits the operator to adjust the volume as appropriate for the particular location.

Figure 6:
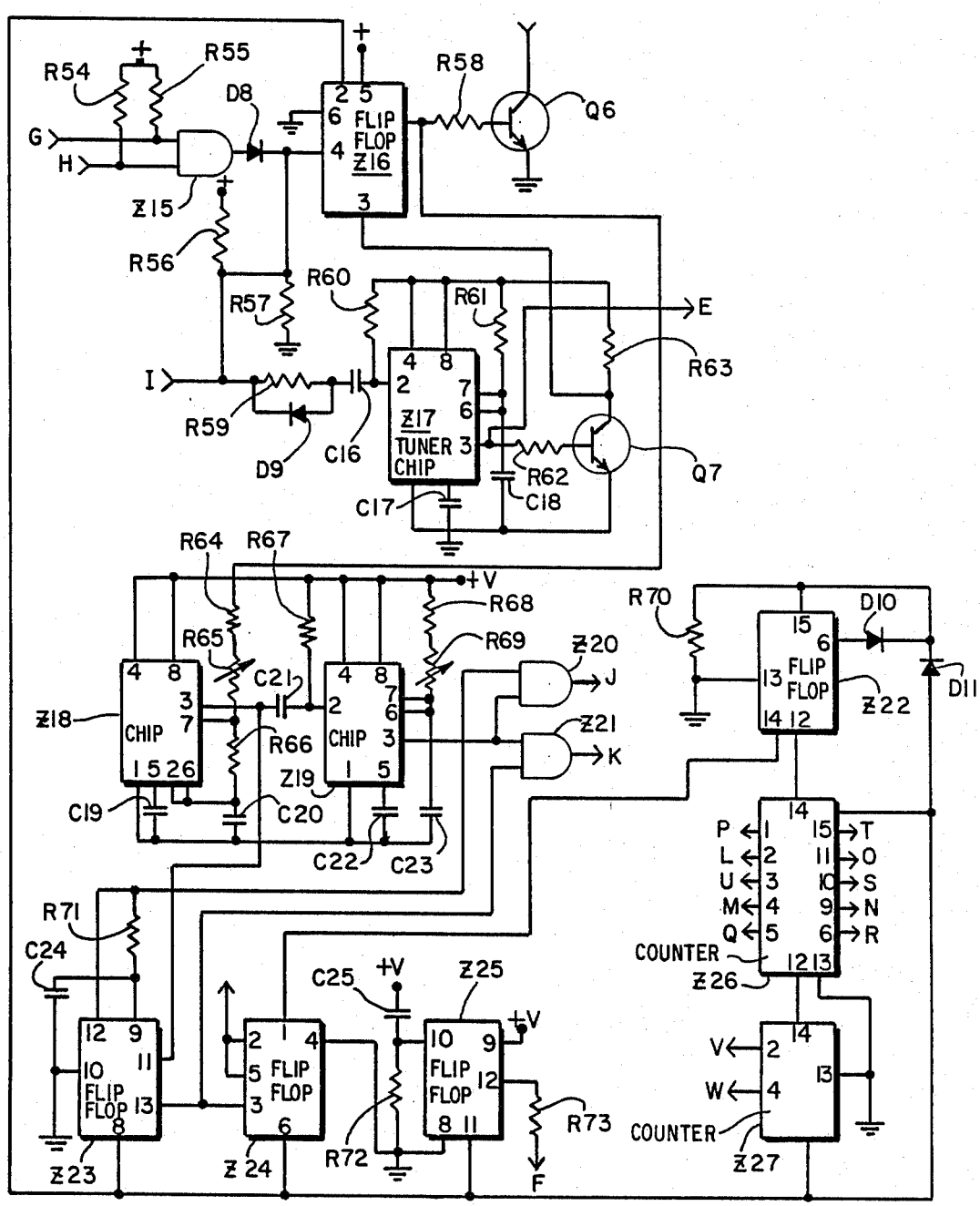
FIG. 6 shows the control circuitry for the EEG-ECT equipment of FIG. 1.

The connection F comes from the control circuitry of FIG. 6. It receives a signal that will turn on the audible EEG after the application of the ECT stimulus.

The connections D and E of FIG. 5 connect to the chip Z14 in order to provide the other audible tones from the instrument during the course of treatment. The latter connection E provides an input that will result in an audible tone during the period that the physician pushes the treatment button but before the actual application of ECT. The upper connection D provides the different tone which emanates from the equipment during the actual ECT application.

In the control circuitry shown in FIG. 6, the connection I leads to the treatment button. The diodes D8 and D9 prevent "bounce", or double action, on a single depression of the button. Depressing the treat button causes the 555 timer chip Z17 to issue a signal which travels to the connection E shown in FIG. 5 to create the one-second warning signal.

The same signal also travels to the flip flop Z16 which, after one second, changes its state to turn on. The output of the flip flop Z16, after amplification, lights a bulb on the equipment during the actual ECT. The leads G and H connect the treatment dial poles through the AND gate Z15 to the flip flop Z16.

The signal from the chip Z17 also travels to the chip Z18 which establishes the stimulation frequency of 140 pulses per second for the ECT.

Furthermore, the signal from the chip Z17 also travels to the chip Z19. There, it sets the width of the ECT stimulus pulse. Each pulse has a width of one millisecond.

The flip flop Z23 changes state with each pulse, causing the ECT stimulus pulse to the patient to alternate between positive and negative. The flip flop Z25 turns on the audible EEG at the end of the ECT stimulus. The flip flops Z22 and Z24 count the pulses of ECT stimulus. The flip flop Z22 also receives the setting on the treatment dial to establish the actual length of the ECT stimulus.

TABLE

Components Used in the Figures

| Identification | Component |
|---|---|
| C1–C4, C13–C15, C17–C22, C24 | .01 μf |
| C5 | 1.0 μf |
| C6, C7 | .033 μf |

TABLE-continued

Components Used in the Figures

| Identification | Component |
| --- | --- |
| C8, C12, C25 | .056 μf |
| C8', C16, C23 | .1 μf |
| C9 | .027 μf |
| C10 | .18 μf |
| C11 | .018 μf |
| C26 | 2600 μf |
| C27, C28, C31 | 1000 μf |
| C29, C30 | 22 μf |
| D1-D4 | 1N4404 |
| D5-D11, D13-D17 | 1N4004 |
| D12 | 1N4734A |
| F1 | 1.5 A |
| F2 | 5 A |
| L1-L3 | CN502 |
| L4, L5 | K301 |
| Q1, Q2 | 2N5566 |
| Q3, Q4, Q6, Q7 | 2N4401 |
| Q5 | 2N4403 |
| Q8 | 2N5401 |
| Q9 | 1RF712 |
| Q10, Q12, Q14 | MJ15024 |
| Q11, Q13 | 1RF511 |
| R1, R2, R14, R15, R29, R31, R43, R44, R47, R50, R53-R55, R57, R62, R70, R78, R79 | 100K Ω |
| R3, R4, R59 | 10 M Ω |
| R5, R6 | 49.9 Ω |
| R7 | 100 Ω |
| R8, R10, R11, R13, R30, R37-R40, R45, R48, R49, R56, R58, R63, R67, R71, R73, R74, R76 | 10K Ω |
| R9, R10, R16, R17, R24, R51 | 1K Ω |
| R18, R27 | 49.9K Ω |
| R19 | 45.2K Ω |
| R20 | 5K Ω |
| R21, R61, R72 | 1 M Ω |
| R22 | 806K Ω |
| R23 | 3.3K Ω |
| R25 | 1.62 M Ω |
| R28, R65 | 50K Ω |
| R32-R34 | 120K Ω |
| R35 | 110K Ω |
| R36 | 102K Ω |
| R41, R60, R66 | 22K Ω |
| R42 | 5.6K Ω |
| R46 | 81K Ω |
| R52 | 2K Ω |
| R64 | 39K Ω |
| R68 | 82K Ω |
| R69 | 20K Ω |
| R75 | .62 Ω, 10 W. |
| R77 | 47K Ω |
| T1 | 241-48-7 |
| T2 | 241-36-6 |
| T3 | 241-24-8 |
| V | LA130-10 |
| Z1-Z10, Z13 | TL074 |
| Z11 | 1CL8038 |
| Z14, Z17-Z19 | MC1455 |
| Z15 | 1N4004 |
| Z16, Z23-Z25 | 4013 |
| Z20, Z21 | 4081 |
| Z22, Z26, Z27 | 4017 |
| Z28, Z29 | BR-62 |
| Z30 | 7815 |
| Z31 | 7915 |

Figure 7:
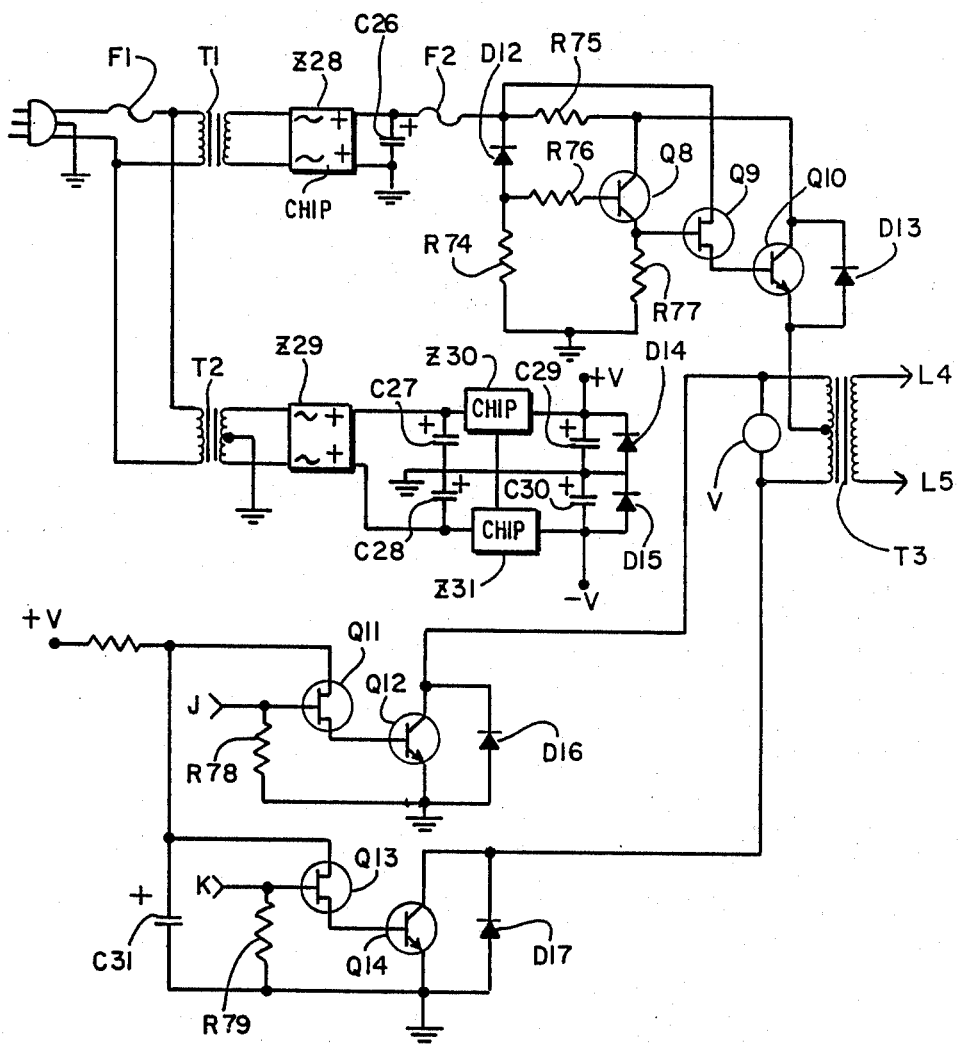
FIG. 7 gives a circuit diagram for the power supply, including the electricity used in the ECT section, of the equipment shown in FIG. 1.

The outputs from the AND gates Z20 and Z21 pass along the leads J and K to the power circuitry of FIG. 7. The signal on these connections control the release of the electrical stimulus for the ECT to the patient.

The power circuitry of FIG. 7 eventually delivers the actual electrical stimulus to the leads L4 and L5 connected to the patient. As discussed before, this section also provides the output at the connection F which, in FIG. 6, triggers the audible EEG. The table shows the components used in the figures.

The percent switch 24 of FIG. 1 has 20 positions. In passing through the first 10 of these positions it, first, connects the lead G of FIG. 6 to the leads L, M, N, O, P, Q, R, S, T, U of the counter Z26. For the eleventh through twentieth positions, it repeats the sequence.

For the first ten positions, the switch 24 leaves the lead H of FIG. 6 unconnected. For positions 11 to 19, the switch 24 connects the lead H to the lead V of the counter Z27. For the twentieth position, the lead H connects to the lead W.

Accordingly, what is claimed is:

1. An electroencephalographic device for use in conjunction with electroconvulsive therapy comprising:
   (A) therapy means for applying electroconvulsive stimulus to a patient;
   (B) detecting means for detecting the brain activity of a patient and conducting, external to that patient, a first electrical signal having an amplitude proportional to the magnitude of the detected brain activity;
   (C) conversion means, coupled to said detecting means, for producing an a.c. second electrical signal having a frequency which is a function of the amplitude of said first signal;
   (D) audible means, coupled to said conversion means, for converting said second electrical signal to an audible signal indicative of the frequency of said second electrical signal;
   (E) control means, coupled to said therapy means and to said audible means, for causing such audible means to produce said audible signal after said therapy means has applied electroconvulsive stimulus to a patient; and
   (F) manually actuable magnitude means, coupled to said therapy means, for changing the magnitude of the electroconvulsive stimulus applied to a patient.

2. The device of claim 1 further including changing means, coupled to said conversion means and said audible means, for when said amplitude of said first electrical signal detected by said detecting means changes, producing a changed audible signal audibly different from the signal produced before the change in said amplitude of said first electrical signal.

3. The device of claim 2 wherein said detecting means includes three leads connectable to a patient, with one of the said leads being a ground lead and being connectable to a part of said patient away from the area of brain activity and with the other two of said leads being measurement leads and being connectable to the patient's head.

4. The device of claim 3 wherein said audible signal has a frequency-modulated waveform having a frequency in the range of about 200 to 1000 Hertz, with the magnitude of the frequency modulation depending upon the amplitude of said first electrical signal.

5. The device of claim 4 wherein said conversion means and said audible means, when said detecting means produces one and another said first electrical signals having different amplitudes, produce one and another of said audible signals having different frequencies from each other.

6. The device of claim 5 wherein said conversion means includes a voltage-controlled oscillator to produce said second electrical signal from said first electrical signal.

7. The device of claim 6 wherein said frequency of said waveform is about 500 Hertz.

8. The device of claim 1 wherein said control means prevents said audible means from producing said second electrical signal while said therapy means applies said electroconvulsive stimulus to a patient.

9. The device of claim 8 further including manually operable initiating means, coupled to said control means, for, upon manual operation, applying electroconvulsive stimulus to a patient and (b) wherein said control means further includes delay means for, after the manual operation of said initiating means, for a predetermined period of time, delaying the application of electroconvulsive stimulus to a patient.

10. The device of claim 9 wherein said audible signal is a first audible signal and said audible means, during the application of electroconvulsive stimulus to a patient, includes means for producing a second audible signal audibly different from said first audible signal.

11. The device of claim 10 wherein said audible means includes means for producing a third audible signal, audibly different from said first and second audible signals, between the time that said initiating means is manually operated and the time that said therapy means applies electroconvulsive stimulus to a patient.

12. The device of claim 11 whereun said detecting means includes three leads connectable to a patient, with one of said leads being a ground lead and for connection to a part of said patient away from the area of brain activity with the other two of said leads being measurement leads and for connection to the patient's head and said detecting means produces said first electrical signal having an amplitude proportional to the difference in the magnitude of the electrical signals produced in said other two leads.

13. The device of claim 12 wherein said conversion means and said audible means includes means for producing an audible tone of a frequency-modulated waveform having a specific frequency in the range of about 200 to 1000 Hertz, with the magnitude of the frequency modulation depending upon the amplitude of said first electrical signal.

14. The device of claim 13 wherein said conversion means and said audible means, when said detecting means produces one and another of said first electrical signals having different amplitudes, includes means for producing one and another of said audible signals having different frequencies from each other.

15. The device of claim 14 wherein said conversion means includes a voltage-controlled oscillator includes means for producing said second electrical signal from said first electrical signal.

16. The device of claim 15 wherein said frequency of said waveform is about 500 Hertz.

17. A method of applying and discerning the effect of electroconvulsive therapy upon a patient comprising:

(A) applying electroconvulsive therapy having a first magnitude upon a patient;

(B) detecting the brain activity of said patient;

(C) producing a first electrical signal having an amplitude proportional to the magnitude of the brain activity detected in the patient;

(D) producing an a.c. second electrical signal having a frequency which is a function of said amplitude of said first electrical signal;

(E) converting said second electrical signal to an audible tone indicative of the frequency of said second electrical signal;

(F) thereafter ascertaining the patient's condition from the audible tone;

(G) appropriately adjusting the therapy magnitude; and (H) applying the adjusted therapy to the patient.

18. The method of claim 17 further including, when said amplitude of said first electrical signal changes, producing an a.c. second electrical signal of a different frequency and converting the a.c. second electrical of a different frequency to an audible signal of a different tone.

19. The method of claim 18 wherein the step of detecting the brain activity of a patient includes connecting a first electrical lead to a part of said patient away from the area of brain activity and two other leads to the patient's head and wherein said first electrical signal has an amplitude proportional to the difference in the magnitude of the electrical signals produced in said two other leads.

20. The method of claim 19 wherein said audible tone produced by the conversion of said electrical signal has a frequency-modulated waveform having a specific frequency in the range of about 200 to 1000 Hertz, with the magnitude of the frequency modulation depending upon the amplitude of said first electrical signal.

21. The method of claim 20 further including not producing said second electrical signal while applying electroconvulsive stimulus to a patient.

22. The method of claim 21 further including manually initiating electroconvulsive therapy to a patient and delaying, after the manual initiating of electroconvulsive stimulus, for a predetermined period of time, the application of electroconvulsive stimulus to a patient.

23. The method of claim 22 wherein said audible signal is a first audible signal and, during the application of electroconvulsive therapy to a patient, further including producing a second audible signal audibly different from said first audible signal.

24. The method of claim 23 further including producing a third audible signal, audibly different from said first and second audible signals, between the time of manually initiating electroconvulsive stimulus and the time of applying electroconvulsive therapy to a patient.

25. The method of claim 24 wherein said frequency of said waveform is about 500 Hertz.

* * * * *